United States Patent [19]

Skoldinov et al.

[11] 4,216,321
[45] Aug. 5, 1980

[54] 3,4-DIHYDROPYRROLO-[1,2-A]-PYRAZINE AND METHOD OF PREPARING SAME

[75] Inventors: Alexandr P. Skoldinov; Arkady M. Likhosherstov; Vitaly P. Peresada; Konstantin O. Chizhov, all of Moscow, U.S.S.R.

[73] Assignee: Nauchno-Issledovatelsky Institut Farmakologii, Moscow, U.S.S.R.

[21] Appl. No.: 891,760

[22] Filed: Mar. 30, 1978

[51] Int. Cl.$^2$ .......................................... C07D 279/30
[52] U.S. Cl. ..................................... 544/349; 544/31
[58] Field of Search ......................................... 544/349

[56] References Cited

U.S. PATENT DOCUMENTS

| | | | |
|---|---|---|---|
| 3,531,485 | 9/1970 | Freed | 544/349 |
| 3,998,820 | 12/1976 | Likhosherstov et al. | 424/247 |
| 4,044,015 | 8/1977 | Kuhla | 544/349 |

FOREIGN PATENT DOCUMENTS 237153 6/1969 U.S.S.R.

OTHER PUBLICATIONS

Rayevskii, et al., "Pharm. Chem. Jour.", (USSR), vol. 10, 1976, pp. 55–58.
Freed, et al., "J. Org. Chem.", vol. 25, 1960, pp. 2108–2113.
Nazarova, "Pharm. Chem. Journ.", (USSR), vol. 10 (1), 1976, pp. 88–92.
Likhosherstov, et al., "Zhurnal Organicheskoi Khim", vol. VI, (N8), 1970, pp. 1729–1734.
Ponomarev, et al., "Poklady Akademii Nauk", (USSR), vol. 148, (N4), 1963, pp. 860–862.

*Primary Examiner*—Donald G. Daus
*Assistant Examiner*—James H. Turnipseed
*Attorney, Agent, or Firm*—Robert E. Burns; Emmanuel J. Lobato; Bruce L. Adams

[57] ABSTRACT

The novel compound according to the present invention, viz. 3,4-dihydropyrrolo-[1,2-a]-pyrazine has the formula:

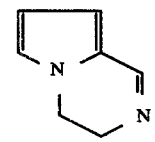

The method of preparing this compound comprises reacting dialkylacetals or dioxalane of a 2,5-dialkoxytetrahydrofurfurol with ethylenediamine in a medium of lower aliphatic acids at a temperature within the range of from 100° to 150° C., followed by isolation of the desired product.

The novel compound according to the present invention, viz. 3,4-dihydropyrrolo-[1,2-a]-pyrazine, owing to a simple method for producing same, simplifies the process of manufacture of physiologically active compounds employed in neuroleptic or coronary dilating preparations, wherein it may be used as the starting material.

4 Claims, No Drawings

3,4-DIHYDROPYRROLO-[1,2-A]-PYRAZINE AND METHOD OF PREPARING SAME

FIELD OF THE INVENTION

The present invention relates to a novel compound, viz. 3,4-dihydropyrrolo-[1,2-a]-pyrazine and a method of preparing this compound which is useful as the starting product in the synthesis of octahydropyrrolo-[1,2-a]-pyrazine and, consequently, in the manufacture of physiologically active compounds such as a coronary dilating preparation 10-{β-[N-(1,4-diazobicyclo-/4,3,0/nonanyl)-propionyl]}-2-chlorophenothiazine dihydrochloride and a neuroleptic agent γ-[N-(1,4-diazobicyclo-/4,3,0/-nonanyl)]propyl-para-fluorophenylketone dihydrochloride.

BACKGROUND OF THE INVENTION

In the prior art methods for the preparation of physiologically active compounds such as 10-{β-[N-(1,4-diazobicyclo-/4,3,0/-nonanyl)propionyl]}-2-chloro-phenothiazine dihydrochloride and γ-[N-(1,4-diazobicyclo-/4,3,0-/-nonanyl)]propyl-parafluoro-phenylketone dihydrochloride use is made of octahydropyrrolo-/1,2-a/-pyrazine which is produced by reduction of hexahydropyrrolo-/1,2-a/-pyrazin-1-one with lithium alumohydride in the medium of diethyl ether. The starting hexahydropyrrolo-/1,2-a/-pyrazin-1-one is prepared by a multi-stage synthesis from 67-chlorovaleric acid which comprises bromination of δ-chlorovaleric acid in the presence of $PCl_3$, esterification of the resulting product, followed by condensation with ethylenediamine. This prior art method has disadvantages residing in the necessity of using a hazardous and rarely-available lithium alumohydride, an inflammable solvent as well as the difficulty of preparing the starting hexahydropyrrolo-/1,2-a/-pyrazin-1-one based on the use of δ-chlorovaleric acid.

Also known in the art is a method of preparing octahydropyrrolo-/1,2-a/-pyrazine by way of a catalytic dehydration of furan diamine. This prior art method has a disadvantage residing in a complicated character of the process of dehydration of N-tetrahydrofurfurylethylenediamine which is effected in a quartz pipe at a temperature within the range of from 300° to 315° C. over alumina activated with zirconia. This process has another disadvantage residing in a low yield of the desired product, i.e. 30%, and, furthermore, it is very difficult to implement the process on a commercial scale.

SUMMARY OF THE INVENTION

It is an object of the present invention to prepare such a novel compound, viz. 3,4-dihydropyrrolo[1,2-a]-pyrazine which would make it possible to prepare, in a simple and efficaceous manner, the above-mentioned physiologically active compounds for which the novel compound is used as the starting material. The novel compound according to the present invention has not been hitherto described in the literature.

This object is accomplished by the provision of a novel compound, viz. 3,4-dihydropyrrolo-/1,2-a/-pyrazine of the formula:

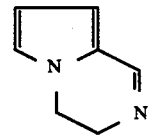

and a method of preparing same by reacting dialkylacetals or dioxalane of 2,5-dialkoxytetrahydrofurfurol with ethylenediamine in the medium of lower aliphatic acids at a temperature within the range of from 100° to 150° C., followed by isolation of the desired product.

In order to minimize the formation of resinous products, the process of interaction of said compounds with ethylenediamine is conducted in the presence of water in an amount of from 0.5 to 2 moles per one mole of ethylenediamine.

DETAILED DESCRIPTION OF THE INVENTION

The novel compound according to the present invention, i.e. 3,4-dihydropyrrolo-/1,2-a/-pyrazine has the formula:

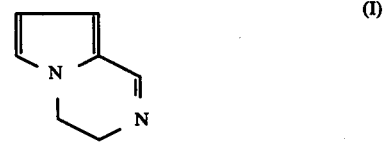

(I)

3,4-dihydropyrrolo-/1,2-a/-pyrazine comprises a colorless liquid with an amine odour and boiling point of 92°–94°/8 mm/, $n_D^{22} = 1.5945$. The structure of this compound is proven, on the one hand, by the data of elemental analysis, and, on the other hand, by the data of PMR- and mass-spectra. In the PMR-spectra there is a singlet at 3.80 m.d. (scale δ, internal standard TMS) corresponding to four protons at $C_3$ and $C_4$ atoms; a multiplet within the range of 6.00–6.37 m.d. corresponding to two protons at $C_7$ and $C_8$ atoms; a multiplet centered at 6.60 m.d. corresponding to one proton at $C_6$; a singlet at 8.07 m.d. corresponding to one proton at $C_1$ atom. The integral curve corresponds, in toto, to eight protons and its appearance is in consistence with the compound formula. Individual character of the compound has been proven by the gas-chromatography method and its molecular weight has been determined by the data of mass-spectrometry which show that M+ has m/e=120.

The method of preparing 3,4-dihydropyrrolo-/1,2-a/-pyrazine according to the present invention comprises treatment solutions of dialkylacetals or dioxalane of 2,5-dialkoxytetrahydrofurfurol in the medium of lower aliphatic acids with an aqueous solution of ethylenediamine for a period of 1 to 5 hours at a temperature within the range of from 100° to 150° C. In doing so, one amino group of ethylenediamine reacts with 2,5-dialkoxytetrahydrofuran system with the formation of pyrrol system, whereas the second amino group of ethylenediamine reacts with the acetal or dioxalane grouping with the formation of a Schiff base. In general, the synthesis of 3,4-dihyropyrrolo-/1,2-a/-pyrazine is effected in accordance with the following scheme:

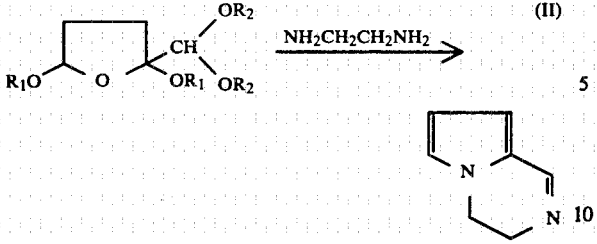

wherein $R_1=R_2=R_3=CH_3$; or $R_1=R_2=R_3=C_2H_5$, or $R_1=CH_3$, $R_2$, $R_3=-CH_2-CH_2-$.

According to the theory, in the method of the present invention one mole of a dialkylacetal or dioxalane of 2,5-dialkoxytetrahydrofurfurol reacts with one mole of ethylenediamine. However, to ensure a more smooth character of the process, it is advisable to use a small excess of ethylenediamine (0.2–0.5 mol.). The process of preparing 3,4-dihydropyrrolo-/1,2-a/-pyrazine may be carried out in the medium of lower aliphatic acids. Acetic acid has proven to be most suitable for this purpose. The weight ratio of the amounts of the starting materials to the amount of a lower aliphatic acid may be varied within a wide range (from 1:3 to 1:15 and more) while the ratio of 1:5 is optimal. Presence of a small amount of water (0.5 to 2 moles per one mole of ethylenediamine) exerts a marked effect on the process. Since in the case of using anhydrous reagents the reaction proceeds less smoothly, there is formed a considerable amount of resinous products and the starting acetals or dioxalane of 2,5-dialkoxytetrahydrofurfurol do not totally enter into the reaction. Though the process is conducted at a temperature within the range of from 100° to 150° C., it is obvious that it may be performed at a lower or even higher temperature with increasing or decreasing rates of reactions according to the principal laws of chemical transformations. Recovery of 3,4-dihydropyrrolo-/1,2-a/-pyrazine from the reaction mass is effected by distilling-off said acid, followed by alkalinization of the residue and isolation of the desired product therefrom by means of an organic solvent. After distilling-off the solvent and distillation, the desired product is obtained in the form of a colorless mobile liquid having amine odor.

The resulting, 3,4-dihydropyrrolo-/1,2-a/-pyrazine may be used as the starting product for the synthesis of physiologically active compounds.

Advantages of the utilization of 3,4-dihydropyrrolo-/1,2-a/-pyrazine as the starting material reside in the possibility of performing the process of preparing octahydropyrrolo-/1,2-a/-pyrazine on a commercial scale. Furthermore, the process for the preparation of 3,4-dihydropyrrolo-/1,2-a/-pyrazine has a simple technology, since as the starting materials for the production of said compound use is made of dialkylacetals or dioxalane of 2,5-dialkoxytetrahydrofurfurol which is prepared from readily available furfurol.

For a better understanding of the present invention, some specific Examples illustrating its embodiments are given hereinbelow.

EXAMPLE 1

To a mixture of 20.6 g of dimethylacetal of 2,5-dimethoxytetrahydrofurfurol and 8.2 g of a 86% aqueous solution of ethylenediamine, under cooling and stirring, there are dropwise added 100 ml of glacial acetic acid. The resulting reaction mass is heated at a temperature within the range of from 100° to 120° C. for two hours. Acetic acid is distilled-off under vacuum. The residue is dissolved in 20 ml of water and alkalized with a 20% aqueous solution of caustic soda to an alkaline reaction and the desired product is extracted with benzene. Benzene is distilled-off and the residue is distilled in vacuum to give 9.9 g (82% of the theoretical value) of 3,4-dihydropyrrolo-/1,2-a/-pyrazine boiling at 92°–94° C./8 mm/$n_D^{22}$=1.5945. Found, %: C, 69.91; H, 6.80; N, 23.45. $C_7H_8N_2$. Calculated, %: C, 69.95; H, 6.71; N, 23.31.

EXAMPLE 2

The procedure described in the foregoing Example 1 is repeated, with the only exception that the reaction is conducted in the medium of propionic acid at a temperature within the range of from 120° to 150° C. 3,4-dihydropyrrolo-/1,2-a/-pyrazine is obtained at the yield of 61% of the theoretical value.

EXAMPLE 3

The process is conducted in a manner similar to that described in the foregoing Example 1, except that 3,4-dihydropyrrolo-/1,2-a/-pyrazine is produced from diacetal of 2,5-diethyoxytetrahydrofurol. There is obtained 3,4-dihydropyrrolo-/1,2-a/-pyrazine with the yield of 70% of the theoretical value.

EXAMPLE 4

To a mixture of 5.1 g of dioxalane of 2,5-dimethoxytetrahydrofurfurol, 1.8 g of a 100% ethylenediamine and 0.3 g of water 25 ml of glacial acetic acid are added upon stirring and cooling. The reaction mass is heated at a temperature within the range of from 120° to 140° C. for 2.5 hours. Avetic acid is distilled-off under vacuum and the residue is dissolved in 5 ml of water and alkalized with a 20% solution of caustic soda to an alkaline reaction, and the desired product is extracted with benzene. Benzene is distilled-off and the residue is distilled in vacuum to give 2.3 g of 3,4-dihydropyrrolo-/1,2-a/-pyrazine with the yield of 77% of the theoretical value.

What is claimed is:

1. 3,4-Dihydropyrrolo-[1,2-a]-pyrazine of the formula:

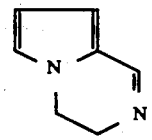

2. A method of preparing 3,4-dihydropyrrolo-[1,2-a]-pyrazine of the formula:

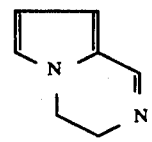

comprising reacting a compound selected from dialkylacetal and dioxalane of 2,5-dialkoxytetrahydrofurfurol with ethylenediamine in a medium of lower aliphatic acids at a temperature within the range of from 100° to 150° C. and then isolating the desired product.

3. A method as claimed in claim 2, wherein the reaction of said compound with ethylenediamine is carried out in the presence of water in an amount of from 0.5 to 2 moles per one mole of ethylenediamine.

4. A method as claimed in claim 2 wherein the reaction of said compound with ethylenediamine is carried out with an excess of said ethylene diamine of about 0.2 to 0.5 mol.

* * * * *